US012570629B2

(12) United States Patent
Kini et al.

(10) Patent No.: US 12,570,629 B2
(45) Date of Patent: Mar. 10, 2026

(54) PROCESS FOR PREPARATION OF IMIDACLOPRID POLYMORPH FORM I

(71) Applicant: UPL LTD, Haldia (IN)

(72) Inventors: Prashant Vasant Kini, Mumbai (IN); Vilas Manikant Mukadam, Mumbai (IN)

(73) Assignee: UPL LTD, Haldia (IN)

( * ) Notice: Subject to any disclaimer, the term of this patent is extended or adjusted under 35 U.S.C. 154(b) by 824 days.

(21) Appl. No.: 17/419,347

(22) PCT Filed: Jan. 22, 2020

(86) PCT No.: PCT/IB2020/050480
§ 371 (c)(1),
(2) Date: Jun. 29, 2021

(87) PCT Pub. No.: WO2020/152592
PCT Pub. Date: Jul. 30, 2020

(65) Prior Publication Data

US 2022/0081414 A1 Mar. 17, 2022

(30) Foreign Application Priority Data

Jan. 23, 2019 (IN) ............................. 201931002861

(51) Int. Cl.
*C07D 401/14* (2006.01)
*C07B 63/00* (2006.01)

(52) U.S. Cl.
CPC ............ *C07D 401/14* (2013.01); *C07B 63/00* (2013.01); *C07B 2200/13* (2013.01)

(58) Field of Classification Search
CPC .................................................. C07B 2200/13
See application file for complete search history.

(56) References Cited

U.S. PATENT DOCUMENTS

| | | | | |
|---|---|---|---|---|
| 5,298,507 | A | 3/1994 | Shiokawa et al. | |
| 6,307,053 | B1 | 10/2001 | Yeh et al. | |
| 6,818,769 | B2 | 11/2004 | Chen | |
| 9,212,162 | B1 * | 12/2015 | Bristow | C07D 401/06 |
| 2015/0368227 | A1 | 12/2015 | Bristow et al. | |

FOREIGN PATENT DOCUMENTS

IN 201621026916 A * 2/2018

OTHER PUBLICATIONS

Monitoring the Polymorphic Transformation of Imidacloprid Usingin Situ FBRM and PVM Zhao et al. Org. Process Res. Dev. 2013, 17, 375-381 (Year: 2013).*
International Search Report and Written Opinion for International Application PCT/IB2020/050480; International Filing Date: Jan. 22, 2020; Date of Mailing: Mar. 25, 2020; 9 pages.
Zhao, J. et al.; "Monitoring the Polymorphic Transformation of Imidacloprid Using in Situ FBRM and PVM"; Organic Process Research & Development, vol. 17, Issue No. 3; 2013; pp. 375-381.

* cited by examiner

*Primary Examiner* — Jeffrey S Lundgren
*Assistant Examiner* — Eric Tran
(74) *Attorney, Agent, or Firm* — CANTOR COLBURN LLP

(57) ABSTRACT

The present invention relates to process for preparation of Form I polymorph of 1-[(6-chloro-3-pyridyl) methyl]-N-nitroimidazolidin-2-ylideneamine (imidacloprid). In particular the present invention relates to process for preparation of Form I of imidacloprid containing dimer impurity≤0.5%.

10 Claims, 2 Drawing Sheets

PROCESS FOR PREPARATION OF IMIDACLOPRID POLYMORPH FORM I

CROSS REFERENCE TO RELATED APPLICATIONS

This application is a National Stage application of PCT/IB2020/050480, filed Jan. 22, 2020, which claims priority to Indian Patent Publication No. 201931002861, both of which are incorporated by reference in their entirety herein.

FIELD OF THE INNOVATION

The present invention relates to process for preparation of polymorph of 1-[(6-chloro-3-pyridyl) methyl]-N-nitroimidazolidin-2-ylideneamine (imidacloprid). In particular the present invention relates to process for preparation of Form I of imidacloprid.

BACKGROUND OF THE INVENTION

Imidacloprid also known as 1-[(6-chloro-3-pyridyl) methyl]-N-nitroimidazolidin-2-ylideneamine represented by formula 1, is a neonicotinoid insecticide used to control sucking insects, termites, some soil insects, and fleas on pets.

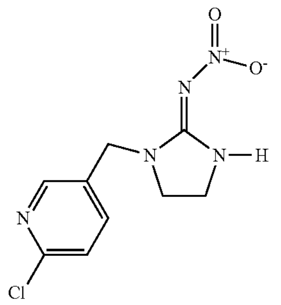 [SMILES: O=[N+]([O-])/N=C1\NCCN1Cc1ccc(Cl)nc1]

It is a broad-spectrum insect neurotoxin with high efficiency and low residue.

U.S. Pat. No. 6,818,769 disclose a process for preparation of heterocyclic diamine single-sided condensation products. This patent also discloses a di-condensation by-product (dimer compound). The process disclosed in this patent can improve yield, minimize double-sided condensation byproduct, and produce high-quality product It has been known that imidacloprid exists in two polymorphic forms of which Form I is thermodynamically stable form and Form II is metastable form (Org. Process Res. Dev. 2013, Vol. 17, Pg. No. 375-381).

Inventors of the present invention found that impurities affect the selective formation of desired polymorphic form. It was observed by the inventors that, the presence of impurities such as dimer compound inhibits formation of the imidacloprid polymorph Form I and leads to formation of metastable form (imidacloprid polymorph Form II) and ultimately results in formation of mixture of imidacloprid polymorph Form I and imidacloprid polymorph Form II. Hence, there is an urgent and unmet need of an efficient process for selectively preparing imidacloprid polymorph Form I.

OBJECTS OF THE INVENTION

It is an object of the present invention to reduce the content of dimer and unreacted reactants present as impurities in imidacloprid.

It is another object of the present invention to provide a process for preparation of pure a crystalline form of Imidacloprid polymorph.

Yet another object of the present invention is to provide a process for purification and selective formation of imidacloprid polymorph Form I.

Thus, the object of the present invention is to prepare Form I of Imidacloprid characterized by a melting point of 145.23±2° C., determined by differential scanning calorimetry (DSC) of FIG. 1.

SUMMARY OF THE INVENTION

In an aspect of the present invention there is provided a process for preparation of imidacloprid Form I.

In another aspect the process for preparation of imidacloprid Form I comprising a) Refinement of imidacloprid and
b) selective crystallisation of imidacloprid polymorph Form I The present invention provides a process for selectively preparing imidacloprid Form I by selective crystallisation of imidacloprid Form I and reducing the impurity content wherein said impurity comprise a compound represented by formula (2) referred herein as dimer impurity.

In another aspect the present invention provides a process for preparing imidacloprid Form I comprising:

Step-1:

a) dissolving Imidacloprid in an organic solvent;
b) cooling the solution at a predetermined rate; and
c) effecting crystallization resulting in imidacloprid having substantially less impurities Step-2:

a) dissolving Imidacloprid obtained from the step-1, in an organic solvent;
b) cooling the solution at a predetermined rate; and
c) effecting crystallization resulting in imidacloprid polymorph Form I Further there is provided a process for selectively preparing imidacloprid polymorph Form I said process comprising the steps of:

a) dissolving Imidacloprid having impurities 0.5% in an organic solvent;
b) cooling the solution at a predetermined rate; and
c) effecting crystallization resulting in imidacloprid polymorph Form I The present invention also provides a process for preparing compositions comprising imidacloprid polymorph Form I having dimer impurity content less than or equal to about 0.5%.

The present invention also provides a process for preparing compositions comprising imidacloprid polymorph Form I having dimer impurity content less than about 0.2%.

There is also provided agrochemical combinations comprising imidacloprid crystalline polymorph Form I produced according to the present process with one or more other pesticides.

Further there is provided agrochemical compositions comprising imidacloprid polymorph Form I produced according to the present process in combination with one or more other pesticides and a process for preparing such compositions.

DETAILED DESCRIPTION OF THE INVENTION

Figure 1:
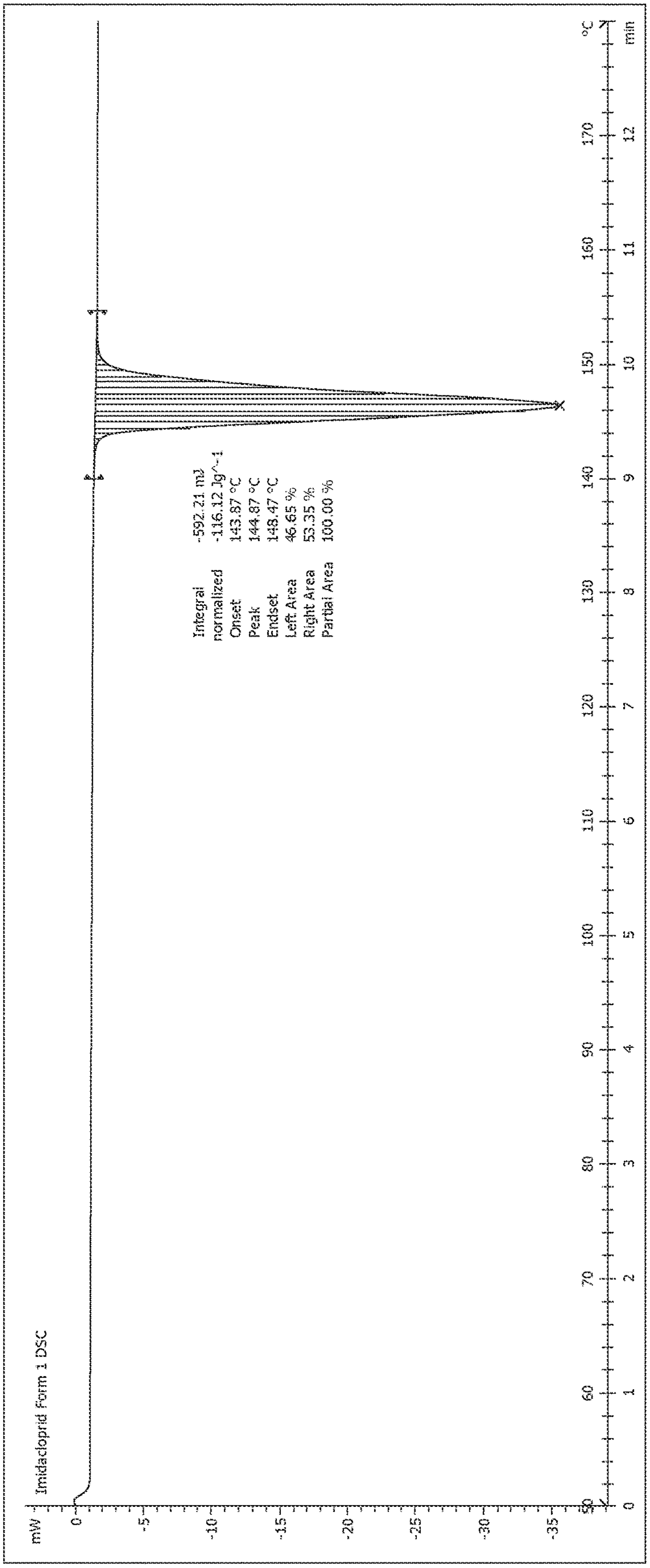
FIG. 1 is a graph of a thermogram obtained by DSC of Form I of imidacloprid prepared according to the present invention.
Figure 2:
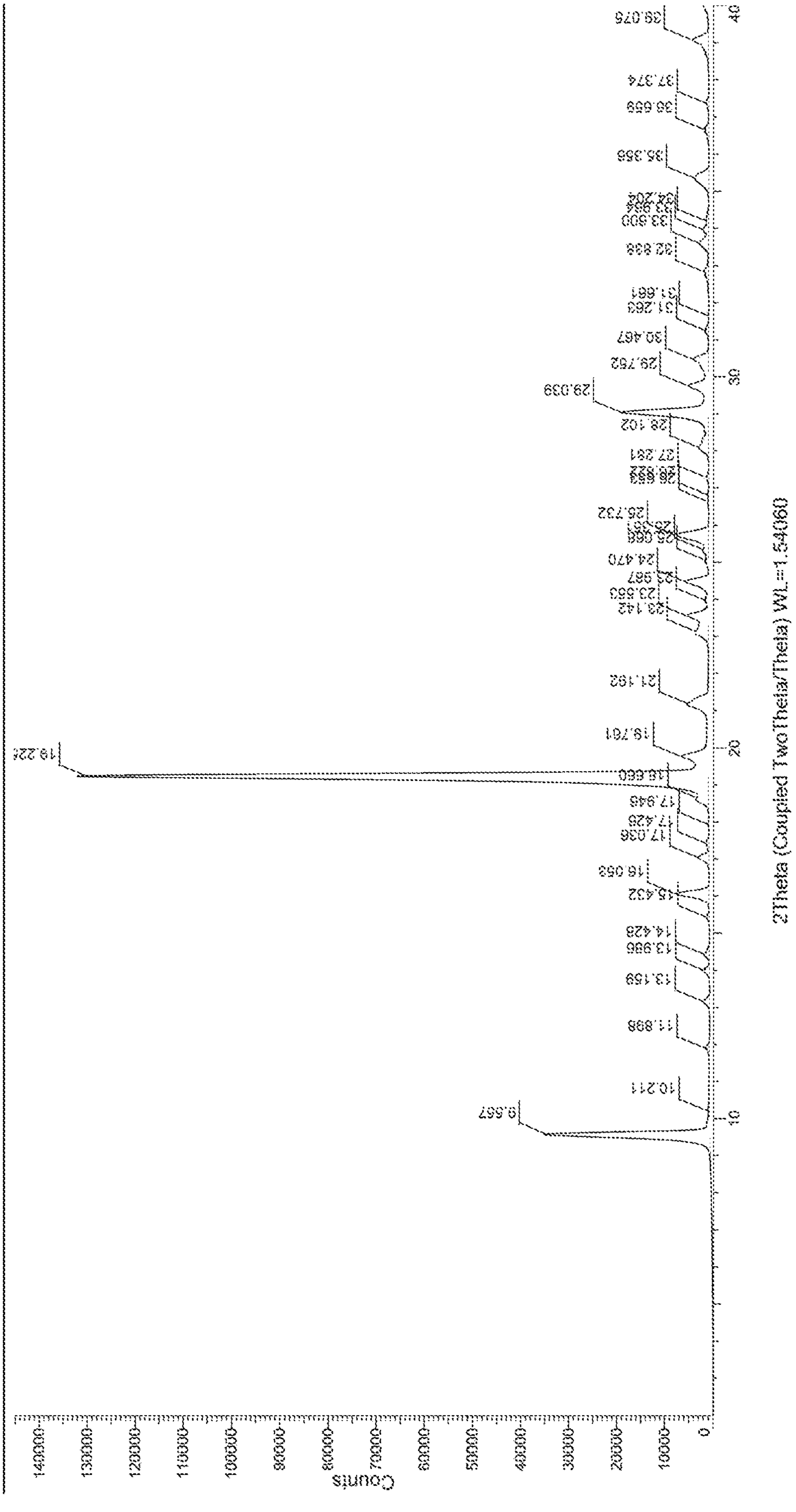
FIG. 2 is the powder X-ray diffraction pattern of the substantially pure Form I crystalline polymorph of imidacloprid prepared according to the present invention.

For the purposes of the following detailed description, it is to be understood that the invention may assume various alternative variations and step sequences, except where expressly specified to the contrary. Moreover, other than in any operating examples, or where otherwise indicated, all numbers expressing, for example, quantities of materials/ingredients used in the specification are to be understood as being modified in all instances by the term "about".

The term "about" shall be interpreted to mean "approximately" or "reasonably close to" and any statistically insignificant variations therefrom.

As used herein, the terms "comprising" "including," "having," "containing," "involving," and the like are to be understood to be open-ended, i.e., to mean including but not limited to. The terms "preferred" and "preferably" refer to embodiments of the invention that may afford certain benefits, under certain circumstances.

In an embodiment, the aspects and embodiments described herein shall also be interpreted to replace the clause "comprising" with either "consisting of" or with "consisting essentially of" or with "consisting substantially of".

Inventors of the present Invention found that the compound imidacloprid synthesized as per U.S. Pat. No. 6,307,053 or by any other known process comprises a mixture of polymorphs, di-condensation by-product represented by the Formula (2) and unreacted reactants as impurities.

Formula (2)

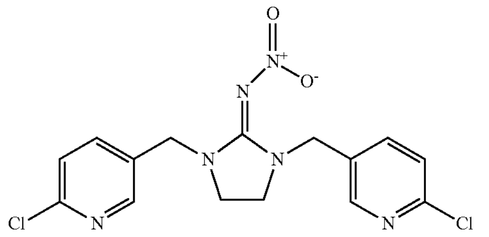

In the present invention, herein after, di-condensation by-product represented by formula (2) is referred to as 'dimer impurity'.

It is surprisingly found by the present inventors that imidacloprid crystalline Form I is prepared in substantially pure form by reducing the dimer impurity in the synthesized imidacloprid. Specifically, the present invention is directed to reduce the content of dimer impurity below 0.5% in the manufactured imidacloprid and/or polymorphic forms thereof in order to obtain the desired substantially pure form of imidacloprid.

With respect to the present disclosure, imidacloprid form I refers to monoclinic Imidacloprid modification I with melting point 145.23±2° C.

With respect to the present disclosure, imidacloprid form II refers to monoclinic Imidacloprid modification I with melting point 137.72±2° C.

In an embodiment the present invention provides imidacloprid Form I having dimer impurity represented by formula (2) content less than or equal to 0.5% w/w.

In an embodiment the present invention provides imidacloprid Form I having dimer impurity represented by formula (2) content less than 0.2% w/w.

In another aspect the present invention provides a process for selectively preparing crystalline polymorph Form I of imidacloprid.

The term, "substantially pure" as used herein refers to a polymorphic form of imidacloprid, Form I or Form II, which is at least about 90% pure. This means that the polymorph of imidacloprid does not contain more than about 10% of any other compound and, in particular, does not contain more than about 10% of any other form of imidacloprid. Preferably, the term "substantially pure" refers to a polymorph of imidacloprid, Form I or Form II, which is greater than about 95% pure. This means that the polymorph of imidacloprid does not contain more than about 5% of any other compound and, in particular, does not contain more than about 5% of any other form of imidacloprid. More preferably, the term "substantially pure" refers to a polymorph of imidacloprid, Form I or Form II; which is greater than about 98% pure, which means that the polymorph of imidacloprid does not contain more than about 2% of any other compound and, in particular, does not contain more than about 1% of any other form of imidacloprid.

Characteristic powder X-ray diffraction pattern peak positions are reported for polymorphs in terms of the angular positions (two theta) with an allowable variability of ±0.1°. The variability of 0.1° is intended to be used when comparing two powder X-ray diffraction patterns.

Accordingly, the process for preparation of substantially pure polymorphs of imidacloprid are described hereinafter.

In an embodiment a process for selectively preparing imidacloprid Form I comprising the steps of:

Step 1: Refinement of imidacloprid; and

Step 2: selective crystallisation of imidacloprid Form I

In another embodiment the process for selectively preparing imidacloprid Form I comprises:

Step 1: refinement of imidacloprid from impurities; and

Step 2: selective reducing the dimer impurity (2) content to less than 0.5% and crystallising pure imidacloprid Form I.

In another embodiment the process for selectively preparing imidacloprid Form I comprises:

Step 1: refinement of imidacloprid from impurities; and

Step 2: selective crystallisation of imidacloprid Form I substantially free from dimer impurity represented by formula (2).

In an embodiment the refinement in step 1) comprises purification of imidacloprid.

In another embodiment step 1) comprises purification of imidacloprid by reducing the impurities content wherein said impurity comprise dimer impurity represented by formula (2).

In another embodiment step 1) comprises purification of imidacloprid from impurities wherein said impurities comprise dimer and starting materials and other by products.

In an embodiment step 1) comprises crystallisation of imidacloprid using suitable solvent to obtain imidacloprid Form I.

In an embodiment imidacloprid of step 1) comprises imidacloprid having mixture of polymorphs and impurities.

In another embodiment imidacloprid of step 1) comprises substantially pure imidacloprid having reduced dimer impurity content.

In yet another embodiment imidacloprid of step 1) has purity about 80% w/w.

In an embodiment imidacloprid of step 1) has purity about 95% w/w.

In another embodiment imidacloprid of step 1) has purity about 98% w/w.

In an embodiment step 2) comprises crystallisation of imidacloprid using suitable solvent to obtain substantially pure imidacloprid Form I.

In another embodiment step 2) comprises selective crystallisation of imidacloprid Form I wherein imidacloprid has purity more than 98% w/w.

The present invention further provides a process for selectively preparing imidacloprid Form I said process comprising the steps of:

Step 1:

a) dissolving Imidacloprid in an organic solvent to obtain a solution;
b) cooling the solution at a predetermined rate; and
c) effecting crystallization resulting in imidacloprid having less impurities Step-2:

a) dissolving Imidacloprid obtained from the step 1 in an organic solvent to obtain a solution;
b) cooling the solution at a predetermined rate; and
c) effecting crystallization resulting in imidacloprid Form I.

In an embodiment the starting compound, imidacloprid of step 1 (a) comprises Imidacloprid having mixture of polymorphs and impurities.

In an embodiment imidacloprid of step 1 (a) comprises imidacloprid Form II and impurities.

In an embodiment imidacloprid of step 1 (a) comprises imidacloprid Form II and dimer impurity represented by formula 2 as one of the impurity.

In an embodiment of the present invention, in step 1 (a) the organic solvent is selected from, but not limited to, alcohols, ethers, aromatic hydrocarbons, ketones, chlorinated solvents, esters, aliphatic hydrocarbons, nitriles, amides, organosulfur solvents, water and mixtures thereof.

In a preferred embodiment of the present invention, organic solvent is selected from, but not limited to, following stated solvents:

alcohols may include methanol, ethanol, isopropyl alcohol, n-butanol, t-butanol, etc. ethers may include diethyl ether, tetrahydrofuran, dioxanes, dibutyl ether, etc.;

aromatic hydrocarbons may include toluene, benzene, xylene, etc.;

ketones may include acetone, MIBK, etc.;

chlorinated solvents may include methylene chloride, dichloromethane, chloroform, dichloroethane, and carbon tetrachloride, etc.;

esters may include ethyl acetate, methyl acetate, etc.;

aliphatic hydrocarbons may include n-Hexane, petroleum ether, etc.;

nitriles may include acetonitrile, etc.;

amides may include N, N-dimethylformamide (DMF), etc.; and organosulfur solvents may include dimethyl sulfoxide (DMSO), etc.

In a preferred embodiment, the organic solvent is selected from alcohols, aliphatic or aromatic hydrocarbons, nitriles, water and mixtures thereof.

In another preferred embodiment, the organic solvent is selected from nitriles and mixture of nitriles optionally with other organic solvents.

In an embodiment of the present invention, the step-1 (a) is carried out at temperature in the range from about 250 to about 120° C.

In an embodiment of the present invention, the step-1 (b), is carried out at temperature in the range from about 20° C. to about 50° C.

In an embodiment of the present invention, the step-1 (b), cooling of Imidacloprid solution is carried out for a period of 15 minutes to 3 hours.

According to an embodiment of the present invention, the step-1 (c) is effected at a temperature in the range from about −15° C. to about 30° C.

According to an embodiment of the present invention, in step-1 (c), the crystallization is effected by sudden cooling.

According to an embodiment of the present invention, in step-1 (c), the crystallization is effected by sudden cooling in less than 15 minutes.

According to an embodiment of the present invention, in step-1 (c), the crystallization is effected by gradual cooling, keeping the solution at a temperature in the range from about −15° C. to about 0° C. for 15 minutes to 3 hours.

In an embodiment of the present invention, the solution is stirred at reflux temperature in organic solvent for 1 hr and then cooled to 20-22° C. at a cooling rate of about 0.3-0.5° C./min.

In an embodiment the organic solvent is acetonitrile.

In an embodiment, the organic solvent is methanol.

According to one embodiment of the present invention, the step-1 (c), the crystallization is optionally initiated by seeding the solution with Imidacloprid having purity≥98% w/w.

In an embodiment of the present invention, in step 1 (c), imidacloprid with less impurities is isolated by filtration or decantation.

In another embodiment, the step 1 (c) provides imidacloprid having dimer impurity represented by formula 2 content reduced to less than or equal to 0.5% w/w.

In another embodiment, the step 1 (c) provides imidacloprid having a mixture of imidacloprid Form I and imidacloprid Form II.

In an embodiment the present invention provides imidacloprid Form I having dimer impurity content represented by formula (2) reduced to less than or equal to 0.5% w/w.

In an embodiment, the step 2) comprises a process for selective crystallization of imidacloprid Form I.

In another embodiment, imidacloprid of step 2 (a) comprises a mixture of imidacloprid Form I and imidacloprid Form II.

In another embodiment, imidacloprid of step 2 (a) comprises a mixture of imidacloprid Form I and imidacloprid Form II optionally obtained as a product of step-1 (c).

In yet another embodiment imidacloprid of step 2 (a) comprises imidacloprid Form II.

In an embodiment of the present invention, in step 2 (a) the organic solvent is selected from, but not limited to the group consisting of alcohols, ethers, aromatic hydrocarbons, ketones, chlorinated solvents, esters, aliphatic hydrocarbons, nitriles, amides, organosulfur solvents, water and mixtures thereof.

In a preferred embodiment, the organic solvent is selected from the group consisting of:

alcohols may include methanol, ethanol, isopropyl alcohol, n-butanol, t-butanol, etc.

ethers may include diethyl ether, tetrahydrofuran, dioxanes, dibutyl ether, etc.

aromatic hydrocarbons may include toluene, benzene, xylene, etc.

ketones may include acetone, MIBK, etc.

chlorinated solvents may include methylene chloride, dichloromethane, chloroform, dichloroethane, and carbon tetrachloride, etc.

esters may include ethyl acetate, methyl acetate, etc.

aliphatic hydrocarbons may include n-Hexane, petroleum ether, etc.

nitriles may include acetonitrile, etc.

amides may include N, N-dimethylformamide (DMF), etc. and organosulfur solvents may include dimethyl sulfoxide (DMSO), etc.

In a preferred embodiment, the organic solvent is selected from the group consisting of alcohols, aliphatic or aromatic hydrocarbons, nitriles, water and mixtures thereof.

In another preferred embodiment, the organic solvent is selected from nitriles and mixture of nitriles optionally with other organic solvents.

In an embodiment of the present invention, the step 2 (a) is carried out at temperature in the range from about 250 to about 120° C.

In an embodiment of the present invention, the step 2 (b) is carried out at temperature in the range from about 20° C. to about 50° C.

In an embodiment of the present invention, the step 2 (b) is carried out for a period of about 15 minutes to 3 hours.

According to an embodiment, the step 2 (c), is performed at temperature in the range from about −15° C. to about 30° C.

According to an embodiment, in step 2 (c) the crystallization is effected by gradual cooling.

In present embodiment, the step 2 (c) is carried out for a period of about 15 minutes to 3 hours.

In an embodiment the solution is stirred at reflux temperature for 1 hr, then cooled to 20-22° C. to form crystals of Form 1 of imidacloprid.

According to one embodiment of the present invention, in step 2 (c), the crystallization is optionally initiated by seeding the solution with imidacloprid Form I having purity≥98% w/w.

In an embodiment of the present invention imidacloprid Form I crystals are isolated in step 2 (c) by filtration.

In another embodiment there is provided a process for selectively preparing imidacloprid Form I comprising:

a) dissolving Imidacloprid having dimer content 0.5% w/w in an organic solvent to obtain a solution;

b) cooling the solution at a predetermined rate; and c) effecting crystallization resulting in imidacloprid Form I In an embodiment Imidacloprid of step a) comprises a mixture of imidacloprid Form I and imidacloprid Form II and having dimer impurity≤0.5% w/w.

In an embodiment imidacloprid of step a) comprises imidacloprid Form II having impurities≤0.5% w/w.

In an embodiment the organic solvent used in step a) is selected from, but not limited to, the group consisting of alcohols, ethers, aromatic hydrocarbons, ketones, chlorinated solvents, esters, aliphatic hydrocarbons, nitriles, amides, organosulfur solvents, water and mixtures thereof.

In a preferred embodiment of the present invention, organic solvent is selected from the group consisting of:

alcohols may include methanol, ethanol, isopropyl alcohol, n-butanol, t-butanol, etc.

ethers may include diethyl ether, tetrahydrofuran, dioxanes, dibutyl ether, etc.

aromatic hydrocarbons may include toluene, benzene, xylene, etc.

ketones may include acetone, MIBK, etc.

chlorinated solvents may include methylene chloride, dichloromethane, chloroform, dichloroethane, and carbon tetrachloride, etc.

esters may include ethyl acetate, methyl acetate, etc.

aliphatic hydrocarbons may include n-Hexane, petroleum ether, etc.

nitriles may include acetonitrile, etc.

amides may include N, N-dimethylformamide (DMF), etc.

organosulfur solvents may include dimethyl sulfoxide (DMSO), etc.

In a preferred embodiment, the organic solvent is selected from alcohols, aliphatic or aromatic hydrocarbons, nitriles, water and mixtures thereof.

In another preferred embodiment, the organic solvent is selected from nitriles and mixture of nitriles optionally with other organic solvents.

In an embodiment the step a) is carried out at temperature in the range from about 250 to about 120° C.

In an embodiment the step b) is carried out at temperature in the range from about 20° C. to about 50° C.

In an embodiment, the step b) is carried out for a period of about 15 minutes to 3 hours.

According to an embodiment, the step c) is carried out at temperature in the range from about −15° C. to about 30° C.

According to an embodiment, in step c), the crystallization is effected by gradual cooling for a period of about 15 minutes to 3 hours.

According to an embodiment, the crystallization in step c) is optionally initiated by seeding the solution with Imidacloprid Form I having purity more than or equal to (≥) 98% w/w.

According to the present invention, imidacloprid comprising a mixture of imidacloprid Form I and imidacloprid Form II and having dimer impurity content≥0.5% undergo purification for reducing the level of dimer impurity and then polymorphic conversion to form Imidacloprid Form 1. It has been unexpectedly found that crystallization of imidacloprid having dimer impurity content≤0.5%, using suitable solvent provides selective formation of desired polymorph of Imidacloprid i.e. Form I.

In the above stated embodiments, the level of dimer compound impurity is a crucial factor in the formation of desired polymorph. As shown in Table 1, mixture of imidacloprid Form I and imidacloprid Form II having dimer content≥0.5% needs a two-step process for the selective formation of desired polymorphic form of imidacloprid i.e. Form I whereas, imidacloprid comprising mixture of Form I and Form II having dimer content≤0.5% needs a one-step process for the selective formation of desired polymorphic form of imidacloprid i.e. Form I.

TABLE 1

| Imidacloprid | | Step 1 (First crystallization) | DSC MP | Step 2 (Second crystallization) | DSC MP |
|---|---|---|---|---|---|
| FORM | Dimer | FORM | (° C.) | FORM | (° C.) |
| 1 + 2 | 2.4% | 2 | 136.5 | 1 | 144.8 |
| 1 + 2 | 1.0% | 2 | 136.5 | 1 | 144.8 |
| 1 + 2 | 0.5% | 1 | 144.8 | — | — |

In above stated embodiment, disclosed a method that provides, in step-2 optionally, a crystalline polymorphic form of imidacloprid is designated Form I. This polymorph is characterised, for example, by DSC.

As shown in FIG. 1, Form I exhibit a differential scanning calorimetry (DSC) thermogram which is characterised by a predominant endotherm peak at 144.87° C.

The invention will now be described further by reference to the following examples, which are intended to illustrate, but not limit, the scope of the appended claims.

EXAMPLES

Example 1

Step 1:

10 g of imidacloprid (purity 97.6% w/w and dimer content 2.4% w/w) was heated in 30 ml of acetonitrile to reflux temperature until complete dissolution of the imidacloprid was observed. The solution was stirred at reflux temperature for 1 hr. The solution was then cooled to 20-22° C. at a cooling rate of about 0.3-0.5° C./min. The crystals of pure imidacloprid formed were filtered out, washed with acetonitrile and dried at 60-65° C. in an oven.

Yield: 80%.

Purity: 98.27% w/w; Dimer content: 0.13% w/w using HPLC.

Step 2

5 g of imidacloprid obtained from step 1 was heated in 10 ml of acetonitrile to reflux temperature until complete dissolution. The solution was stirred at reflux temperature for 1 hr. The solution was then cooled to 20-22° C. The crystals of Form 1 of imidacloprid formed were filtered and dried at 60-65° C. in an oven.

Yield: 93%.

Purity by HPLC: 98.46% w/w, dimer content: 0.04%

DSC endotherm peak: 144.87° C.

Example 2

Step 1:

10 g of imidacloprid (purity 98.5% and dimer content 1.5%) was heated in 40 ml of acetonitrile to reflux temperature until complete dissolution of the imidacloprid was observed. The solution was stirred at reflux temperature for 1 hr. The solution was then cooled to 20-22° C. at a cooling rate of about 0.3-0.5° C./min. The crystals of pure imidacloprid formed were filtered out, washed with acetonitrile and dried at 60-65° C. in an oven.

Yield: 79%.

Purity by HPLC: 98.39% w/w; dimer content: 0.31% w/w).

Step 2:

5 g of imidacloprid obtained from step 1 was heated in 10 ml of acetonitrile to reflux temperature until complete dissolution. The solution was stirred at reflux temperature for 1 hr. The solution was then cooled to 20-22° C. The crystals of Form 1 of imidacloprid formed were filtered out and dried at 60-65° C. in an oven.

Yield: 92%.

Purity by HPLC: 98.58% w/w; dimer content: 0.15% w/w; DSC endotherm peak at: 146.3° C.

Example 3

Step 1:

10 g of imidacloprid (having purity 98.2% and dimer content 1.8%) was heated in 30 ml of methanol to reflux temperature until complete dissolution of the imidacloprid was observed. The solution was stirred at reflux temperature for 1 hr. The solution was then hot filtered at 45-50° C. The crystals of pure Imidacloprid formed were filtered out and dried at 60-65° C. in an oven.

Yield: 81%.

Purity by HPLC: 98.52%, dimer content: 0.18% w/w).

Step 2:

5 g of imidacloprid obtained from step 1 was heated in 10 ml of acetonitrile to reflux temperature until complete dissolution. The solution was stirred at reflux temperature for 1 hr. The solution was then cooled to 20-22° C. The crystals of Form 1 of imidacloprid formed were filtered out and dried at 75-85° C. in an oven.

Yield: 93.8%.

Purity by HPLC: 99.74% w/w; dimer content: 0.11% w/w; DSC endotherm peak: 143.3° C.

The invention claimed is:

1. A process for preparing imidacloprid Form I comprising:

step-1:

a) dissolving imidacloprid in a first organic solvent to provide a solution;

b) cooling the solution of step-1a); and c) effecting crystallization from the cooled solution resulting in imidacloprid having substantially less impurities; and step-2:

a) dissolving the imidacloprid obtained from the step-1c, in a second organic solvent to provide a solution;

b) cooling the solution of step 2a) at a predetermined rate; and c) effecting crystallization from the cooled solution of step 2b);

wherein said first organic solvent is selected from nitriles and second organic solvents are selected from ethers, aromatic hydrocarbons, ketones, esters, aliphatic hydrocarbons, nitriles, amides, organosulfur solvents, and mixtures thereof;

wherein said process provides imidacloprid Form I having a purity of at least 98%, and having an impurity of dimer represented by Formula (2) of less than or equal to 0.5% w/w.

Formula (2)

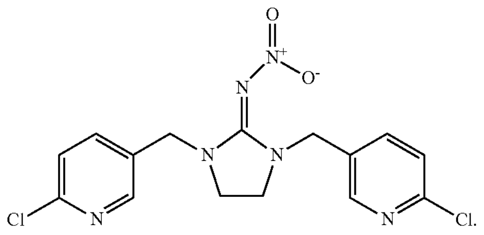

2. The process according to claim 1 wherein, said second organic solvents are selected from aliphatic or aromatic hydrocarbons, nitriles, and mixtures thereof.

3. The process according to claim 1, wherein said first and second organic solvents are both acetonitrile.

4. The process according to claim 1, wherein step-1a) is carried out at temperature in the range from about 25° C. to about 120° C., step-1b) is carried out at temperature in the range from about 20° C. to about 50° C., or step-1c) crystallization is effected by sudden or gradual cooling.

5. The process according to claim 1, wherein the imidacloprid of step-1a) comprises imidacloprid Form II comprising the dimer impurity represented by Formula (2)

Formula (2)

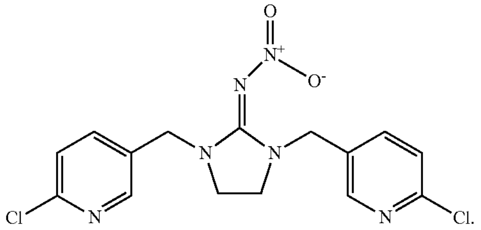

6. The process according to claim 1, wherein step 2a) is carried out at temperature in the range from about 25° C. to about 120° C., step 2b) is carried out at temperature in the range from about 20° C. to about 50° C., step 2c) is carried out at temperature in the range from about −15° C. to about 30° C., or step 2c) crystallization is effected by gradual cooling.

7. The process according to claim 1, wherein the imidacloprid of step 2a) comprises imidacloprid Form II or a mixture of imidacloprid Form I and imidacloprid Form II.

8. A process for selectively preparing imidacloprid polymorph Form I comprising:

a) dissolving imidacloprid having impurity of dimer represented by Formula (2) of less than 0.5% in an organic solvent to provide a solution;

b) cooling the solution of step a); and c) effecting crystallization of the cooled solution of step b);

wherein said organic solvent is selected from ethers, aromatic hydrocarbons, ketones, esters, aliphatic hydrocarbons, nitriles, amides, organosulfur solvents, and mixtures thereof; and wherein said process provides imidacloprid Form I having a purity of at least 98%, and having an impurity of dimer represented by Formula (2) of less than or equal to 0.5% w/w, Formula (2)

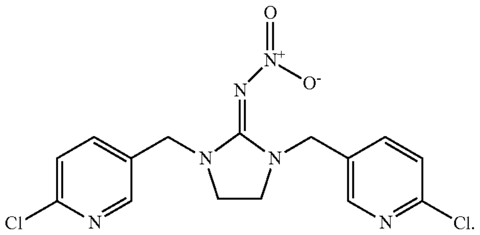

9. The process according to claim 8, wherein said organic solvent is selected from, aliphatic or aromatic hydrocarbons, nitriles, and mixtures thereof.

10. The process according to claim 1, wherein:

the nitrile is acetonitrile;

the ethers are selected from the group consisting of diethyl ether, tetrahydrofuran, dioxanes, and dibutyl ether;

the aromatic hydrocarbons are selected from the group consisting of toluene, benzene, and xylene;

the ketones are selected from the group consisting of acetone and methyl isobutyl ketone (MIBK);

the esters are selected from the group consisting of ethyl acetate and methyl acetate;

the aliphatic hydrocarbons are selected from the group consisting of n-hexane and petroleum ether;

the amide is N,N-dimethylformamide (DMF); and the organosulfur solvent is dimethyl sulfoxide (DMSO).

* * * * *